(12) United States Patent
Gross et al.

(10) Patent No.: US 10,265,428 B1
(45) Date of Patent: Apr. 23, 2019

(54) REFLECTOR SYSTEM FOR A LIGHTING ASSEMBLY

(71) Applicant: THE BOEING COMPANY, Chicago, IL (US)

(72) Inventors: Adam Franklin Gross, Santa Monica, CA (US); Shanying Cui, Calabasas, CA (US); Brian Wayne Neff, Solana Beach, CA (US); Kevin Geary, Santa Monica, CA (US); Andrew C. Keefe, Encino, CA (US); Randolph C. Camp, III, Kirkland, WA (US); Kevin S. Callahan, Shoreline, WA (US); Jamie J. Childress, Mercer Island, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 15/726,595

(22) Filed: Oct. 6, 2017

(51) Int. Cl.
| | | |
|---|---|---|
| *A61L 2/10* | (2006.01) | |
| *F21V 7/05* | (2006.01) | |
| *B64D 11/04* | (2006.01) | |
| *B64D 11/02* | (2006.01) | |

(52) U.S. Cl.
CPC .................. *A61L 2/10* (2013.01); *F21V 7/05* (2013.01); *B64D 11/02* (2013.01); *B64D 11/04* (2013.01)

(58) Field of Classification Search
CPC ...................................... A61L 2/10; F21V 7/05
See application file for complete search history.

(56) References Cited

U.S. PATENT DOCUMENTS

| | | | |
|---|---|---|---|
| 3,819,929 A | 6/1974 | Newman | |
| 4,242,725 A * | 12/1980 | Douma | F21V 7/005 362/217.06 |
| 4,388,675 A | 6/1983 | Lewin | |
| 5,062,030 A * | 10/1991 | Figueroa | F21V 7/005 362/241 |
| 6,323,601 B1 | 11/2001 | Klein | |
| 6,988,816 B2 * | 1/2006 | Witkowski | F21V 7/005 362/263 |
| 2014/0140888 A1 | 5/2014 | Neister | |
| 2015/0136521 A1* | 5/2015 | Swinkels | E04C 2/324 181/290 |
| 2016/0102820 A1* | 4/2016 | Chang | F21K 9/64 362/84 |
| 2017/0202991 A1 | 7/2017 | Childress | |
| 2017/0299289 A1* | 10/2017 | Brais | F28G 13/00 |

FOREIGN PATENT DOCUMENTS

| | | |
|---|---|---|
| EP | 3225549 | 10/2017 |
| GB | 2009384 | 6/1979 |
| JP | S63187221 | 11/1988 |

OTHER PUBLICATIONS

U.S. Appl. No. 62/461,415, filed Feb. 21, 2017.
Machine translation of JP S63187221.
Extended European Search Report for EP 18198065.7-1015, dated Mar. 4, 2019.

* cited by examiner

*Primary Examiner* — Eliza W Osenbaugh-Stewar (74) *Attorney, Agent, or Firm* — Joseph M. Butscher; The Small Patent Law Group, LLC

(57) ABSTRACT

A lighting assembly includes a light source, such as an ultraviolet (UV) light source that is configured to emit UVC light, and a reflector system including a base having an internal central crest that is configured to direct emitted light away from the light source.

21 Claims, 4 Drawing Sheets

REFLECTOR SYSTEM FOR A LIGHTING ASSEMBLY

FIELD OF THE DISCLOSURE

Embodiments of the present disclosure generally relate to lighting assemblies, and, more particularly, to ultraviolet (UV) light-emitting assemblies having reflector systems that are configured to efficiently direct UV light onto a surface.

BACKGROUND OF THE DISCLOSURE

Commercial aircraft are used to transport passengers between various locations. A typical commercial aircraft includes one or more lavatories within an internal cabin.

Systems are currently being developed to disinfect or otherwise sanitize surfaces within aircraft lavatories that use ultraviolet (UV) light. It has been found that far UV light efficiently disinfects exposed surfaces within a lavatory. UVC light is also used to disinfect exposed surfaces.

In order to effectively sanitize a surface within a lavatory, a UV lighting assembly may be fixed in close proximity to the surface. For example, a UV lighting assembly may be spaced from a toilet within a lavatory a distance of less than one foot.

Many UV light sources are relatively large and bulky, and may be difficult to integrate into a confined space of an aircraft lavatory. As an example, known UV light assemblies include parabolic reflectors having diameters that are substantially larger than UV light sources. The relatively large reflectors occupy significant space. As can be appreciated, however, space within an aircraft is limited, and certain UV light assemblies may be too large to integrate into a particular area of the aircraft.

Further, the process of manufacturing curved reflectors is often time and labor intensive, and even more so for reflectors that are to be used with UV light sources, particularly at UVC wavelengths (200-280 nm). Overall, known reflectors used with UVC wavelengths are made of reflecting materials that are formed in a curved shape.

Known reflectors typically do not reflect UV light away from a light source. For example, a standard T-6 fluorescent tube is a gas filled tube. As such, light reflected back to the bulb can still exit the bulb. However, a UV bulb has a metal rod therein that prevents or otherwise inhibits light from passing therethrough.

SUMMARY OF THE DISCLOSURE

A need exists for a reflector system for a UV lighting assembly that is configured to more uniformly reflect light onto a surface. Further, a need exists for an efficient and compact reflector system for a UV lighting assembly that may be integrated into a confined space, such as within a lavatory of an aircraft. Also, a need exists for a UV lamp reflector that reduces light reflected back into a bulb while increasing an amount of light that is directed out of the reflector.

With those needs in mind, certain embodiments of the present disclosure provide a lighting assembly that includes a reflector system including a base having an internal central crest that is configured to direct emitted light away from a light source. The light source is disposed within the reflector system. In at least one embodiment, the light source is configured to emit ultraviolet (UV) light, such as UVC light. The central crest inhibits light emitted from the light source from reflecting back into the light source.

The central crest is behind the light source. The light source is disposed between the central crest and a light outlet passage of the reflector system. In at least one embodiment, the central crest and the light source are aligned along a central plane of the reflector system.

The lighting assembly may also include a retaining member that securely couples the light source to the central crest.

In at least one embodiment, the base is W-shaped. In at least one embodiment, the base includes outer reflector panels, and inner reflector panels connected to the outer reflector panels. The inner reflector panels downwardly angle from outer ends towards a central longitudinal plane and directly connect at the central crest. The outer ends of the inner reflector panels connect to inner ends of the outer reflector panels at elevated peaks.

The reflector system further may also include opposed side reflector panels flanking the base. Further, the reflector system may include end panels at opposite ends.

In at least one embodiment, the base is formed from a single substrate.

In at least one embodiment, a length of the reflector system is greater than a width of the reflector system.

Certain embodiments of the present disclosure provide a method of manufacturing a lighting assembly. The method includes forming a reflector system. The forming includes forming a base having an internal central crest that is configured to direct emitted light away from a light source.

DETAILED DESCRIPTION OF THE DISCLOSURE

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular condition may include additional elements not having that condition.

Certain embodiments of the present disclosure provide a lighting assembly including a reflector system that is configured to efficiently direct light from a light source onto a surface. The reflector system is configured to redirect light from the light source isotropically around the light source (such as a cylindrical UVC lamp) to uniformly irradiate a surface in order to eliminate microorganisms on the surface. The reflector system is easier to manufacture than known curved reflectors.

A UVC light source may include one or more cylindrical tube lamps that emit light isotropically around the tube. The reflector system redirects light emitted from the UVC light source onto a target surface to increase UV light intensity.

The reflector system includes a plurality of planar (that is, not parabolic or curved) reflector panels. In at least one embodiment, a group of multi-faceted reflector panels are positioned around a light source (such as a tubular UVC lamp). The reflector panels direct emitted light out of the lighting assembly while minimizing or otherwise reducing light from being directed back to the lamp.

Certain embodiments of the present disclosure provide an apparatus for directing light generated by a UV light source. The apparatus includes a plurality of planar reflector panels arranged in a W shape to form a base, and side reflector panels flanking opposing sides of the base and extending from an end of the base. The planar reflector panels are angled relative to one another such that light generated by the UV light source is substantially directed away from the UV light source and towards the side reflector panels.

The apparatus may include a retaining member, such as a socket, that is configured to hold the UV light source proximate to a central crest of the W-shaped base. In at least one embodiment, the retaining member holds the UV light source such that a center of the UV light source is approximately 1.5 inches from the central crest of the W-shaped base.

The UV light source may be a KrCl excimer lamp, a downshifting excimer lamp, an excimer laser, a UVC light emitting diode, a Hg vapor lamp, and/or the like.

The apparatus may also include a cover plate coupled to the side reflectors. The cover plate may be formed of amorphous silica, quartz, metal fluorides having approximately 95% or more transmission at approximately 220 nm, a CYTOP Type S fluoropolymer having approximately 93% to 95% transmission at approximately 220 nm, a Solaflon fluoropolymer having approximately 85% transmission at approximately 220 nm, a PCTFE (PolyChloroTriFluoroEthylene) based material having approximately 90% transmission at approximately 220 nm, and/or the like.

In at least one embodiment, end reflector panels are coupled to opposite ends of the W-shaped base. The planar reflector panels and the side reflector panels may be coated with a layer of Aluminum, such as a layer that is approximately 0.062 inches thick. Optionally, the layer may have a thickness greater or less than 0.062 inches. The Aluminum may be vacuum deposited onto the panels. In at least one embodiment, the panels themselves are formed of Aluminum. The apparatus may also include a layer of one or more of $MgF_2$, $SiO_2$, or $Al_2O_3$ deposited on top of the Aluminum.

Figure 1:
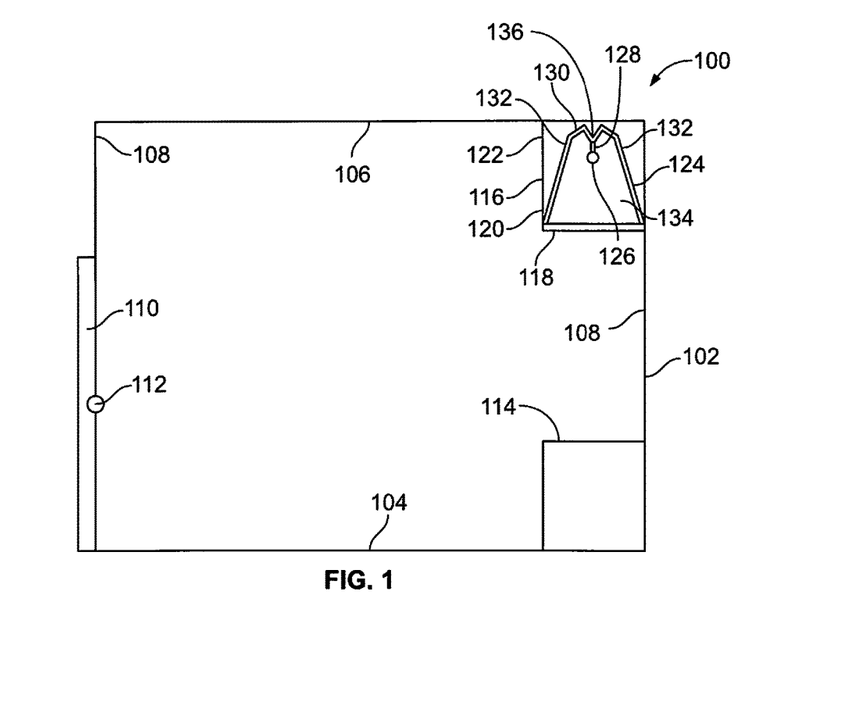
FIG. 1 illustrates a schematic diagram of a UV light sanitizing system for an enclosed space, according to an embodiment of the present disclosure.

FIG. 1 illustrates a schematic diagram of a UV light sanitizing system 100 for an enclosed space 102, according to an embodiment of the present disclosure. The enclosed space 102 may be defined by a floor 104, a ceiling 106, and walls 108 extending between the floor 104 and the ceiling 106. A door 110 may be moveably secured to one of the walls 108. The door 110 may include a lock 112 that is configured to securely lock the door 110 in a closed position. When the lock 112 is in a locked position, the door 110 is unable to be opened. When the lock 112 is in an unlocked position, the door 110 may be opened.

The enclosed space 102 may be a confined space onboard a commercial aircraft. For example, the enclosed space 102 may be a lavatory onboard an aircraft. As another example, the enclosed space 102 may be a galley onboard an aircraft. As yet another example, the enclosed space 102 may be a passenger area onboard an aircraft. The enclosed space 102 may or may not include the door 110. The enclosed space 102 may be within various other vehicles, structures, and/or the like. For example, the enclosed space 102 may be a room within a commercial, municipal, or residential building, or a room onboard a train, bus, ship, or the like.

The enclosed space 102 may include at least one component 114 to be sanitized (for example, disinfected, sterilized, or otherwise cleaned) after use. For example, the component 114 may be a toilet, countertop, sink, floor, cabinet, wall, and/or the like within a lavatory of an aircraft.

The UV light sanitizing system 100 includes a lighting assembly 116, which may be secured to the ceiling 106. For example, the lighting assembly 116 may extend below the ceiling 106, mount above, on, or under a cabinet or countertop, or the like. In at least one other embodiment, a light outlet passage 118 (such as an open end, aperture, clear window, or the like) is flush with or recessed within a lower surface of the ceiling 106. Optionally, the lighting assembly 116 may be secured to (or supported by) various other structures of the enclosed space 102, such as the floor 104, walls 108, a portion of the component 114, or the like.

The lighting assembly 116 includes a housing 120, which may include opaque outer walls 122 connected to the light outlet passage 118. The housing 120 retains a reflector system 124 and a light source 126. The light source 126 may be secured to the housing 120 through fasteners, brackets, or other such mounting features. In at least one embodiment, the light source 126 is secured to the reflector system 124 through at least one retaining member 128, such as a socket(s), a bracket(s), a fastener(s), a guide track(s), rail(s), a clasp(s), a sleeve(s), and/or the like. In at least one embodiment, the light source 126 is not mounted to the central crest 136 or another portion of the reflector system 124, but may be mounted to an external support structure (such as a rack, wall, bracket, beam, and/or the like).

The light outlet passage 118 may be or include a transparent cover or window, such as formed of transparent plastic, glass, or the like, that is configured to allow light emitted from the light source 126 to pass therethrough. The light outlet passage 118 may be a cover or window formed of one or more inorganic materials, fluoropolymers, and/or saturated hydrocarbons, such as UV grade amorphous silica, quartz, metal fluorides such as $MgF_2$, CYTOP Type S fluoropolymer, Solaflon fluoropolymer, PCTFE, and/or the like. Optionally, the light outlet passage 118 may not include a cover or window, but may instead be an open space.

The reflector system 124 includes a base 130 connected to opposed side reflector panels 132 flanking the base 130. The reflector system 124 may also include end panels 134 (only one end panel 134 is shown in FIG. 1) at opposite ends of the reflector system 124.

The base 130 is formed having a W-shape (an inverted W-shape, as shown in FIG. 1) having an internal central crest 136. The retaining member 128 may couple to the central crest 136 to securely retain the light source 126 to the reflector system 124 below the central crest 136. The central crest 136 is behind the light source 126. Thus, the light source 126 is in front of the central crest 136. The light source 126 is disposed between the central crest 136 and the light outlet passage 118. The W-shaped base 130 allows light emitted from the light source 126 to reflect isotropically around the light source 126 and out of the light outlet passage 118. It has been found that the W-shaped base 130 prevents or otherwise inhibits light emitted from the light source 126 from reflecting back into the light source 126. As such, the W-shaped base 130 including the central crest 136 increases the efficiency of the lighting assembly 116 in that all of substantially all light emitted from the light source 126 is directed out of the light outlet passage 118, instead of being directed back into the light source 126. The light emitted out of the lighting assembly 116 is directed onto a surface of the component 114, for example. In at least one embodiment, the light source 126 may be a UV light source that emits sanitizing UV light onto the surface of the component.

The light source 126 may include one or more UV light elements, such as an arc lamp(s), laser(s), light emitting diode(s) (LEDs), microfilament(s), fiber optic element(s), bulb(s), and/or the like. In at least one embodiment, the light source 126 emits the UV light as far UV light that is used to sanitize the component 114. Optionally, the UV light may be UVA light, UVB light, UVC light, vacuum UV light, or the like. In at least one embodiment, the light source 126 may include UV light elements that are configured to emit UV light with different UV bands (for example, at different wavelengths and different frequencies). For example, one UV light element may be configured to emit far UV light, while another UV light element may be configured to emit UVB light.

Figure 2:
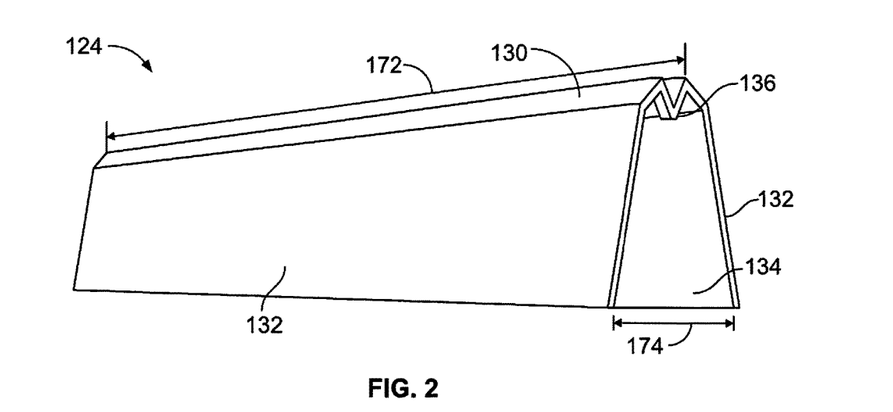
FIG. 2 illustrates a perspective side view of a reflector system, according to an embodiment of the present disclosure.

FIG. 2 illustrates a perspective side view of the reflector system 124, according to an embodiment of the present disclosure. The base 130 connects to the opposed side reflector panels 132. The reflector system 124 may be formed from a single substrate, such as a planar sheet of Aluminum and/or an Aluminum alloy, which is bent and formed as shown. Optionally, the substrate may be formed of various other metals and/or reflective materials. The side reflector panels 132 are flat, planar sheets. Optionally, the side reflector panels 132, the end panels 134, and the base 130 may be separately formed and secured to one another, such as through bonding, fasteners, and/or the like. Alternatively, the reflector system 124 may not include the end panels 134.

Figure 3:
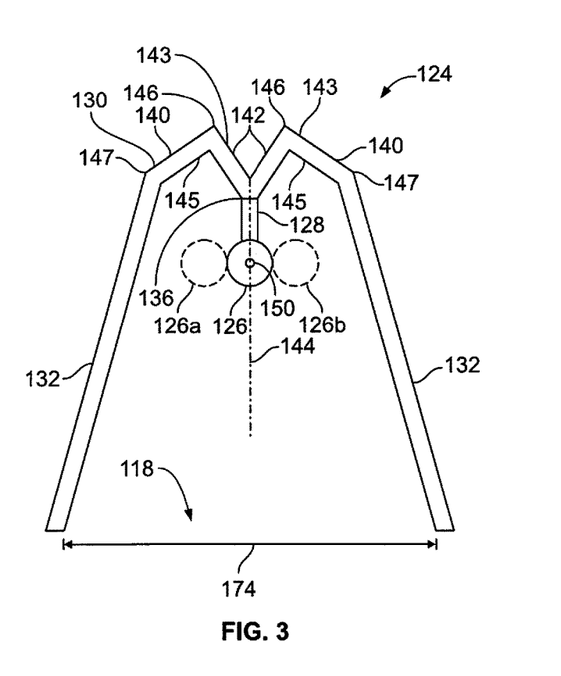
FIG. 3 illustrates an end view of a light source secured to a reflector system, according to an embodiment of the present disclosure.

FIG. 3 illustrates an end view of the light source 136 secured to the reflector system 124, according to an embodiment of the present disclosure. The base 130 includes a W-shape (or inverted W-shape, as shown in FIG. 3) having outer reflector panels 140 that connect to inner reflector panels 142. The outer reflector panels 140 and the inner reflector panels 142 are planar sheets of material. For example, the outer reflector panels 140 and the inner reflector panels 142 may be flat sheets of metal, such as Aluminum and/or Aluminum alloys.

The inner reflector panels 142 downwardly angle from outer ends 143 towards a central longitudinal plane 144 and directly connect at the central crest 136, such as a lower apex or edge. As shown, the outer ends 143 are at an elevated height as compared and in relation to the central crest 136.

The outer ends 143 of the inner reflector panels 142 connect to inner ends 145 of the outer reflector panels 140 at elevated peaks 146, such as upper apexes or edges. The outer reflector panels 140 downwardly angle away from the central longitudinal plane 144 towards outer ends 147. The side reflector panels 132 downwardly and outwardly flare from the outer ends 147 of the outer reflector panels 140 away from the central longitudinal plane 144. Optionally, the side reflector panels 132 may be parallel with the central longitudinal plane 144.

As shown, the light source 126 may be positioned directly below the central crest 136. A central longitudinal axis 150 of the light source 126 may be within the central longitudinal plane 144. That is, the light source 126 and the central crest 136 may be aligned with the central longitudinal plane 150 or another common plane and/or axis.

The central crest 136 provides an edge, apex, or angled junction that directs emitted light away from the light source 126. That is, light emitted by the light source 126 into the central crest 136 reflects away from the light source 126, such as onto interior reflecting surfaces of the outer reflector panels 140, the inner reflector panels 142, and/or the side reflector panels 132. Emitted light that reflects off the outer reflector panels 140, the inner reflector panels 142 and the side reflector panels 132 is directed out of the light outlet passage 118. In this manner, light emitted by the light source 126 is not directed back into the light source 126, thereby promoting efficient light generation.

Further, during operation of the light source 126, it has been found that the W-shaped base 130 effectively widens the light source 126 by producing two virtual light sources 126a and 126b on either side of the light source 126. That is, the W-shaped base 130 causes light generated by the light source 126 to appear to be emanating from a widened volume defined by the light source 126 and the virtual light sources 126a and 126b on either side of the light source 126. The W-shaped base 130 creates shadow images (that is, the virtual light sources 126a and 126b), thereby effectively leading to a wider source of light.

The W-shaped base 130 reflects light emitted by the light source 126 towards the side reflector panels 132, which, in turn, redirect the light out of the light outlet passage 118 and onto a surface of a component. An angle between interior surfaces of an outer reflector panel 140 and an inner reflector panel 142 may be between 90-150 degrees, for example. Further, an angle between exterior surfaces of the inner reflector panels 142 may be between 90-150 degrees, for example. Optionally, the angles may be less than 90 degrees or greater than 150 degrees.

Also, it has been found that the reflector system 124 reflects light emitted from the light source 126 uniformly onto a surface, such as a surface of the component 114 (shown in FIG. 1). The uniform distribution of UV light onto the surface leads to uniform and effective disinfection of the surface.

Figure 4:
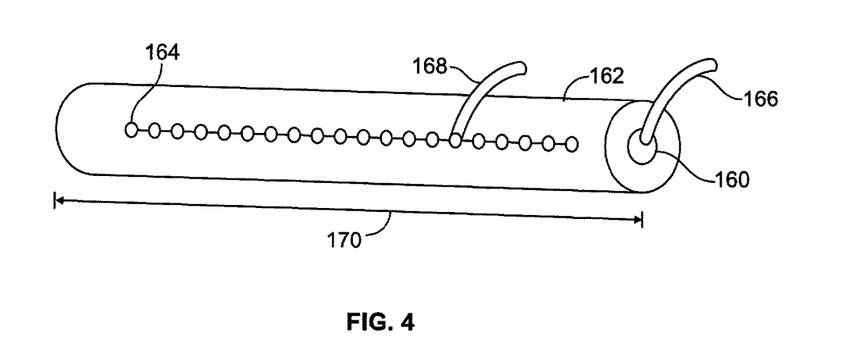
FIG. 4 illustrates a perspective side view of a light source, according to an embodiment of the present disclosure.

FIG. 4 illustrates a perspective side view of the light source 126, according to an embodiment of the present disclosure. The light source 126 may include a central metal tube 160 coupled to a cylindrical sleeve 162 containing one or more light emitting elements 164. An inner electrode 166 connects to the tube 160, while an outer electrode 168 connects to the light emitting elements 164. In at least one embodiment, the light source 126 is a UV light source that is configured to emit UVC light. For example, the light source 126 may be or include an excimer lamp (such as a KrCl excimer lamp that emits light at a wavelength of 222 nm), a downshifting excimer lamp (such as a Xe excimer lamp that emits light at a wavelength of 172 nm that is downshifted to 220-290 nm with a phosphor), an excimer laser, one or more UVC light emitting diodes (LEDs), a Hg vapor lamp that emits light at a wavelength of 254 nm, and/or the like. The light source 126 may include a quartz tube, or optionally, have an inner reflector (for example, a dielectric stack on quarts or reflective aluminum) on an inside of the tube, in order to increase the isotropic emission outwards onto the interior reflecting surfaces of the reflector system 124 (shown in FIGS. 1-3).

In at least one embodiment, the light source 126 includes a quartz tube within a hollow tube. The cross-section of the light source 126 may be donut-shaped. A metal tube may be disposed within hollow tube. The metal tube may act as or otherwise provide an inner electrode. The outside of the quartz tube may have a mesh sleeve that acts as or otherwise provides an outer electrode. A gas (such as KrCl or Xe) is contained within the quartz tube. Applying a high voltage between the inner and outer electrodes results in light emission.

Optionally, the light source 126 may be sized and shaped differently than shown in FIG. 4. For example, the light source 126 may include a plurality of UV light emitting elements 164 (such as light emitting diodes) that are mounted onto the base 130 (shown in FIGS. 1-3). In at least one other embodiment, the light source 126 may be configured to emit other types of UV light, such as far UV light. Alternatively, the light source 126 may be configured to emit light other than UV light, such as ultraviolet light, infrared light, white light, and/or the like.

Referring to FIGS. 1-4, the light source 126 has a length 170 that is the same or substantially the same as the length 172 of the reflector system 124. The light source 126 fits within the reflector system 124 such that the side reflector panels 132 are closer to the light source 126 as compared to a parabolic or curved reflector. The width 174 of the reflector system 124 is substantially less than that of a parabolic or curved reflector, thereby allowing the lighting assembly 116 to fit within smaller volumes of space. Notably, the longitudinal and lateral axes of a curved or parabolic reflector are generally the same. In contrast, the width 174 of the reflector system 124 may be substantially less than the length 172, and may be directly proportional to a length and diameter (or width) of the light source 126, thereby providing a compact reflector system 124 that more closely corresponds to a shape of the light source 126.

Compared to prior known reflectors, the reflector system 124 is easy to manufacture. For example, a substrate (such as single piece of metal, such as Aluminum) may be bent and formed to provide the planar surface of the W-shaped base 130 and the side reflector panels 132. Simple, flat panels may be formed during a fabrication process, as opposed to curved surfaces. The flat panels provide a high degree of reflectivity. For example, it is has been found that vacuum deposition of Aluminum on flat panels provides increased reflectivity. The flat panels allow for improved Aluminum deposition thereon, which leads to greater reflectivity.

Figure 5:
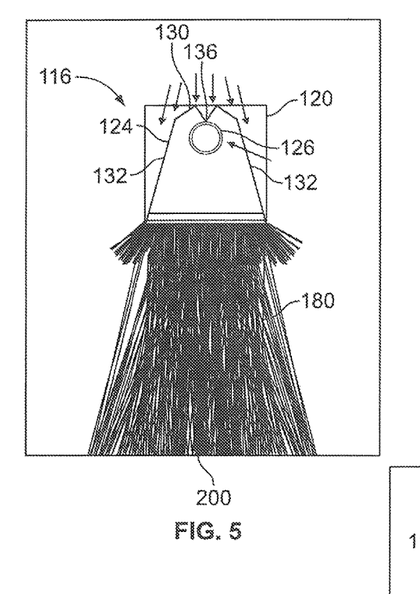
FIG. 5 illustrates an end view of a lighting assembly emitting light onto a surface of a component, according to an embodiment of the present disclosure.

FIG. 5 illustrates an end view of the lighting assembly 116 emitting light 180 onto a surface of a component 200, according to an embodiment of the present disclosure. The light source 126 is within the reflector system 124, such as at a distance of less than 2 inches, for example, as measured from the center of the light source 126 to the center crest 136. In at least one embodiment, the base 130 and the side reflector panels 132 (as well as the end panels 134 shown in FIGS. 1 and 2) are formed of a high reflectivity metal, such as Aluminum, or highly diffuse reflectors such as fluoropolymers. As shown in FIG. 5, the light source 126 may be positioned directly over a center of the component 200.

Figure 6:
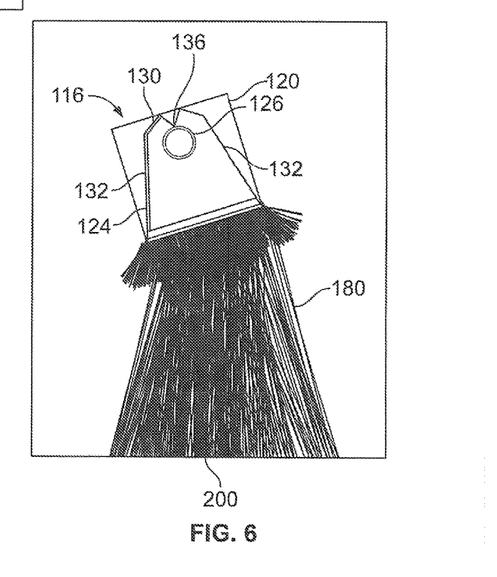
FIG. 6 illustrates an end view of a lighting assembly emitting light onto a surface of a component, according to an embodiment of the present disclosure.

FIG. 6 illustrates an end view of the lighting assembly 116 emitting light 180 onto a surface of a component 200, according to an embodiment of the present disclosure. As shown in FIG. 6, the light source 126 may not be directly over the center of the component 200. The light flux on the component 200 may be adjusted by the angle of the lighting assembly 116 in relation to the component 200.

Referring to FIGS. 1-6, to increase the reflectivity of the reflector system 124, high purity Aluminum may be vacuum deposited onto reflecting surfaces thereof. For example, the reflector system 124 may be formed from a substrate of 6061 mirror-like polished aluminum, other polished metal surfaces, glass, and/or the like, and formed as described above. A center portion may be bent into the W shape to form the base 130. High purity Aluminum may then be vacuum deposited onto the reflecting surfaces.

The reflector system 124 may be vacuum deposited with Aluminum, and include a protective coating, such as $MgF_2$. The reflector system 124 may be formed from a sheet of fluoropolymer, such as polytetrafluoroethylene (PTFE) with 70% reflectivity between 220 nm-290 nm, a porous sheet made of sintered PTFE with 92% diffuse reflectivity, a machined block of sintered PTFE, such as Spectralon fluoropolymer of 90% diffuse reflectivity over the 220 nm to 290 nm UV-C wavelength band, a dielectric distributed Bragg reflector stack that reflects at 220 nm, a higher-order high-reflectivity (HR) dielectric multi-layer coating that achieves simultaneous high reflectivity of more than one narrowband wavelength or high reflectivity over a broadband wavelength range (for example, 220 nm to 255 nm, 250 nm to 290 nm, 220 nm to 290 nm), and/or the like.

In at least one embodiment, the light source 126 may include one or more UVC lamps. For example, the light source 126 may include two UVC light lamps connected in series, or parallel.

Figure 7:
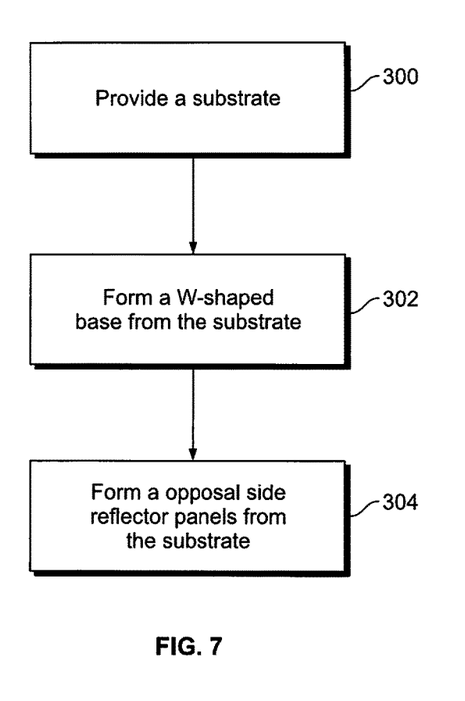
FIG. 7 illustrates a flow chart of a method of forming a reflector system of a lighting assembly, according to an embodiment of the present disclosure.

FIG. 7 illustrates a flow chart of a method of forming a reflector system of a lighting assembly, according to an embodiment of the present disclosure. The method begins at 300, at which a substrate is provided. The substrate is a planar sheet of material, such as a metal. In at least one embodiment, the substrate is a flat piece of Aluminum.

At 302, a W-shaped base is formed from the substrate. In at least one embodiment, a planar sheet may be cut from the substrate, and the planar sheet may be formed (such as through bending) into the W-shaped base. In at least one other embodiment, a portion of the substrate itself may be formed into the W-shaped base.

At 304, opposed side reflector panels are also formed from the substrate on sides of the W-shaped base. For example, separate planar sheets may be cut from the substrate and attached to the W-shaped base, such as through bonding, fasteners, and/or the like. In at least one other embodiment, the substrate is formed (such as through bending) to form the opposed side reflector panels off the previously-formed W-shaped base.

As described herein, embodiments of the present disclosure provide a reflector system for a UV lighting assembly that is configured to uniformly reflect light onto a surface. Further, embodiments of the present disclosure provide an efficient and compact reflector system for a UV lighting assembly that may be integrated into a confined space, such as within a lavatory of an aircraft. Also, embodiments of the present disclosure provide a UV lamp reflector that reduces light reflected to a light source while increasing an amount of light that is directed out of the reflector.

While various spatial and directional terms, such as top, bottom, lower, mid, lateral, horizontal, vertical, front and the like may be used to describe embodiments of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A lighting assembly comprising:
a reflector system including a base connected to opposed planar side reflector panels having exposed ends flanking the base, wherein the base comprises:
an internal central crest that is configured to direct emitted light away from a light source;
planar outer reflector panels; and
planar inner reflector panels directly connected to the outer reflector panels, wherein the inner reflector panels downwardly angle from outer ends towards a central longitudinal plane and directly connect at the central crest, wherein the outer ends of the inner reflector panels connect to inner ends of the outer reflector panels at elevated peaks, and wherein the outer reflector panels directly connect to the side reflector panels.

2. The lighting assembly of claim 1, further comprising the light source disposed within the reflector system, wherein the light source is configured to emit ultraviolet (UV) light.

3. The lighting assembly of claim 2, wherein the central crest inhibits light emitted from the light source from reflecting back into the light source.

4. The lighting assembly of claim 2, wherein the central crest is behind the light source, wherein the light source is disposed between the central crest and a light outlet passage of the reflector system, wherein the central crest and the light source are aligned along a central plane of the reflector system.

5. The lighting assembly of claim 2, further comprising a retaining member that securely couples the light source to the central crest.

6. The lighting assembly of claim 1, wherein the base is W-shaped.

7. The lighting assembly of claim 1, wherein the reflector system further comprises end panels at opposite ends.

8. The lighting assembly of claim 1, wherein the base is formed from a single substrate.

9. The lighting assembly of claim 1, wherein a length of the reflector system is greater than a width of the reflector system.

10. The lighting assembly of claim 1, wherein the reflector system is vacuum deposited Aluminum and includes a protective coating.

11. The lighting assembly of claim 1, wherein the reflector system is formed of a sheet of polytetrafluoroethylene (PTFE) with ≥70% reflectivity between 220 nm-290 nm.

12. The lighting assembly of claim 1, wherein the reflector system is formed of a porous sheet made of sintered polytetrafluoroethylene (PTFE) with 92% diffuse reflectivity.

13. The lighting assembly of claim 1, wherein the reflector system is formed of a dielectric distributed Bragg reflector stack that reflects at 220 nm.

14. The lighting assembly of claim 1, wherein the reflector system is formed of a higher-order high-reflectivity (HR) dielectric multi-layer coating that achieves simultaneous high reflectivity of more than one narrowband wavelength or high reflectivity over a broadband wavelength range.

15. A method of manufacturing a lighting assembly, the method comprising:
forming a reflector system, wherein the forming comprises forming a base connected to opposed planar side reflector panels having exposed ends flanking the base, wherein the base includes an internal central crest that is configured to direct emitted light away from a light source, wherein the forming comprises:
directly connecting planar inner reflector panels to planar outer reflector panels, wherein the inner reflector panels downwardly angle from outer ends towards a central longitudinal plane and directly connect at the central crest, wherein the outer ends of the inner reflector panels connect to inner ends of the outer reflector panels at elevated peaks; and
directly connecting the outer reflector panels to the side reflector panels.

16. The method of claim 15, further comprising disposing the light source within the reflector system, wherein the light source is configured to emit ultraviolet (UV) light.

17. The method of claim 15, further comprising disposing the central crest behind the light source, wherein the disposing comprises disposing the light source between the central crest and a light outlet passage.

18. The method of claim 15, further comprising aligning the central crest and the light source along a central plane of the reflector system.

19. The method of claim 15, further comprising securing coupling the light source to the central crest with a retaining member.

20. The method of claim 15, wherein the forming comprises shaping the base as a W.

21. A lighting assembly comprising:
   an ultraviolet (UV) light source that is configured to emit UVC light;
   a reflector system including a W-shaped base having an internal central crest that is configured to direct emitted light away from a light source, opposed flat side reflector panels having exposed ends flanking the base, and flat end panels at opposite ends, wherein the UV light source is disposed within the reflector system, wherein the central crest inhibits light emitted from the light source from reflecting back into the light source, wherein the central crest is behind the light source, wherein the light source is disposed between the central crest and a light outlet passage of the reflector system, wherein a length of the reflector system is greater than a width of the reflector system; and
   a retaining member that securely retains the light source.

* * * * *